United States Patent [19]
Schmidt et al.

[11] Patent Number: 5,942,402
[45] Date of Patent: *Aug. 24, 1999

[54] METHOD OF DETECTING AND TREATING CANCER

[75] Inventors: Carl J. Schmidt, Exton; Frank Tobin, Broomall; Francis E. Wilkinson, Malvern, all of Pa.

[73] Assignee: SmithKline Beecham Corporation, King of Prussia, Pa.

[*] Notice: This patent is subject to a terminal disclaimer.

[21] Appl. No.: 09/226,548

[22] Filed: Jan. 7, 1999

Related U.S. Application Data

[63] Continuation of application No. 08/879,723, Jun. 20, 1997, abandoned, which is a continuation-in-part of application No. 08/714,744, Sep. 16, 1996, Pat. No. 5,757,264, which is a continuation-in-part of application No. 08/691,479, Aug. 2, 1996, abandoned.

[51] Int. Cl.$^6$ .......................... C07K 16/00; G01N 33/53; G01N 33/567; C12Q 1/00

[52] U.S. Cl. .................. 435/7.1; 435/4; 435/7.2; 435/7.21; 435/7.23; 435/7.92; 530/350; 530/388.1

[58] Field of Search .................. 435/7.1, 4, 7.2, 435/7.21, 7.23, 7.92; 530/350, 388.1

[56] References Cited

PUBLICATIONS

Yamashita et al (Br. J. Cancer, 69:1166–11700), 1994.

*Primary Examiner*—Paula K. Hutzell
*Assistant Examiner*—Susan Ungar
*Attorney, Agent, or Firm*—Law Offices of Jane Massey Licata

[57] ABSTRACT

The present invention provides a new method for diagnosing and treating cancers or BPH. Further provided are therapeutic agents and pharmaceutical compositions for treating cancers and BPH.

1 Claim, No Drawings

METHOD OF DETECTING AND TREATING CANCER

RELATED APPLICATION

This application is a continuation of U.S. Ser. No. 08/879,723 filed Jun. 20, 1997, now abandoned which is a continuation-in-part application of U.S. Ser. No. 08/714,744, filed Sep. 16, 1996, now U.S. Pat. No. 5,757,264 which is also continuation-in-part of U.S. Ser. No. 08/691,479, filed Aug. 2, 1996, now abandoned. The above mentioned patent applications are hereby incorporated by reference in their entirety.

FIELD OF THE INVENTION

This invention relates, in part, to newly developed assay for diagnosing cancers, particularly prostate cancer, and benign prostate hyperplasia (BPH), and methods for identifying agents which modulate $PLA_2$ activity and therapeutic agents that modulate $PLA_2$ activity for treating cancers and BPH.

BACKGROUND OF THE INVENTION

Cancer of the prostate is the most prevalent malignancy in adult males, excluding skin cancer, and is an increasingly prevalent health problem in the United States. In 1994, it was estimated that in the U.S., 38,000 deaths resulted from this disease, indicating that prostate cancer is second only to lung cancer as the most common cause of death in the same population. If diagnosed and treated early, when the cancer is still confined to the prostate, the chances of cure is significantly higher. Accordingly, there is a great need for sensitive methods for the detection of organ-confined prostate cancer.

Extracellular Phospholipase $A_2$ ($PLA_2$) enzymes appear to mediate a variety of responses including cellular proliferation, chemotaxis and inflammation. There are two major groups of extracellular $PLA_2$ enzymes: pancreatic or group I and rheumatoid arthritis synovial fluid (RASF) or group II. The group I enzyme functions in digestion and also in modulating proliferation and chemotaxis. Currently, RASF-$PLA_2$ is predominantly thought to play a role in inflammatory responses including arthritis, septic shock and lung injury. The level of RASF-$PLA_2$ is regulated at the mRNA level by a variety agents including interleukin-6, interleukin-1 and tumor necrosis factor, all of which are involved in inflammatory responses. While elevated levels of $PLA_2$ enzyme activity have been reported in a prostate cancer tissue in rats (F. H. Faas et al., *The Journal of Urology*, Vol 156, 243–248, 1996), there do not appear to be any reports of alterations of RASF-$PLA_2$ mRNA or polypeptide level in prostate cancer or benign prostate hyperplasia in humans.

Northern blot analysis was done on equivalent amounts of mRNA isolated from prostate cancer (PC), benign prostatic hyperplasia (BPH) and normal prostate (NP) according to methods published in Maniatis (*MOLECULAR CLONING* Maniatis, et. al., Cold Spring Harbor Laboratory, Cold Spring Harbor, N.Y.). Probe was synthesized from the full length cDNA encoding RASF-$PLA_2$. Results indicated the following ratios of RASF-$PLA_2$ mRNA: 10:0.25:1 for PC, BPH and NP, respectively. Loading differences were normalized using actin mRNA levels. The result showed that RASF-$PLA_2$ appears to be upregulated in prostate cancer and potentially downregulated in BPH.

As used hereinbelow "$PLA_2$" refers to group II or RASF-$PLA_2$.

SUMMARY OF THE INVENTION

Toward these ends, and others, it is an object of the present invention to provide a new method for diagnosing, treating, and monitoring progression, remission or recurrence of various forms of abnormal cell growth, such as cancers, particulary prostate cancer, and benign prostate hyperplasia (BPH). Further provided are methods to screen for therapeutic agents and pharmaceutical compositions for treating abnormal cell growth, such as cancers, particularly prostate cancer, and BPH. Further provided is the utilization of such agents or compositions for the for the treatement of cancer, patricularly prostate cancer, and BPH.

Thus, in accordance with one aspect of the present invention there are provided methods of screening for compounds which bind to and inhibit activation of the $PLA_2$.

In accordance with another aspect of the present invention there is provided a method of using such inhibiting compounds for treating conditions associated with over-expression of the $PLA_2$.

In accordance with yet another aspect of the present invention, there are provided $PLA_2$ antagonists (inhibitors). Among the preferred antagonists are those which mimic $PLA_2$ so as to bind to $PLA_2$ binding molecules but not elicit a $PLA_2$ -induced response or more than one $PLA_2$-induced response. Also among the preferred antagonists are molecules that bind to or interact with $PLA_2$ so as to inhibit an effect of $PLA_2$ or more than one effect of $PLA_2$ or which prevent expression of $PLA_2$.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DESCRIPION OF THE INVENTION

The present invention relates to diagnostic assays, both quantitative and qualitative for detecting levels of $PLA_2$ protein or $PLA_2$ mRNA in cells, tissues and bodily fluids, including determination of normal and abnormal levels. Thus, for instance, a diagnostic assay in accordance with the invention for detecting over-expression of $PLA_2$ protein compared to normal control bodily fluids or tissue samples may be used to detect the presence of cancers, including prostate cancer. Further, the present method of quantifying protein $PLA_2$ protein level is particularly useful for discriminating between BPH and prostate cancer, since the existing methods such as prostatic specific antigen (PSA), digital examination, and transurethral ultrasound tests have difficulty discriminating between prostate cancer and BPH. For example, the existing PSA diagnostic tests detect 20–28% of BPH patients and 62–81% of prostate cancer patients with PSA blood levels above approximately 99% of the normal population. Assay techniques that can be used to determine levels of gene expression, such as $PLA_2$ of the present invention, in a sample derived from a host are well-known to those of skill in the art. Such assay methods include radioimmunoassays, reverse transcriptase PCR (RT-PCR) assays, immunohistochemistry assays, in situ hybridization assays, competitive-binding assays, Western Blot analyses and ELISA assays. Among these, ELISAs are frequently preferred to detect a gene's expressed protein in biological fluids. An ELISA assay initially comprises preparing an antibody, if not readily available from a commercial source, specific to $PLA_2$, preferably a monoclonal antibody. In addition a reporter antibody generally is prepared which binds specifically to $PLA_2$. The reporter antibody is attached to a detectable reagent such as radioactive, fluorescent or enzymatic reagent, for example horseradish peroxidase enzyme or alkaline phosphatase.

To carry out the ELISA, antibody specific to $PLA_2$ is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time $PLA_2$ binds to the specific antibody attached to the polystyrene dish. Unbound sample is washed out with buffer. A reporter antibody specifically directed to $PLA_2$ and linked to horseradish peroxidase is placed in the dish resulting in binding of the reporter antibody to any monoclonal antibody bound to $PLA_2$. Unattached reporter antibody is then washed out. Reagents for peroxidase activity, including a colorimetric substrate are then added to the dish. Imobilized peroxidase, linked to $PLA_2$ antibodies, produces a colored reaction product. The amount of color developed in a given time period is proportional to the amount of $PLA_2$ protein present in the sample. Quantitative results typically are obtained by reference to a standard curve. Without Uniting the instant invention, typically, for a quantitative diagnostic assay a positive result indicating the disease is one in which blood levels are higher than three standard deviations above the mean blood level for a normal healthy population of individuals (99.86% of the population).

A competition assay may be employed wherein antibodies specific to $PLA_2$ attached to a solid support and labeled $PLA_2$ and a sample derived from the host are passed over the solid support and the amount of label detected attached to the solid support can be correlated to a quantity of $PLA_2$ in the sample.

Nucleic acid methods may be used to detect $PLA_2$ mRNA as a marker for BPH and cancer, particularly prostate cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific rRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones arrayed on a grid (i.e. gridding) can be used to both detect the expression of and quantitate the level of expression of that gene. In this approach, a cDNA encoding the $PLA_2$ gene is fixed to a substrate. The substrate may be of any suitable type including but not limited to glass, nitrocellulose, nylon or plastic. DNA encoding the $PLA_2$ clone is attached to the substrate and then incubated with the analyte, which may be RNA or a complementray DNA (cDNA) copy of the RNA, isolated from the tissue of interest. Hybridization between the substrate bound clone and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

The above tests can be carried out on samples derived from patients' bodily fluids and tissue extracts (homogenates or solubilized tissue) such as from blood, urine, saliva, tissue biopsy and autopsy material.

ANTIBODIES

The $PLA_2$ polypeptide, its fragments or other derivatives, or analogs thereof, or cells expressing them can be used as an immunogen to produce antibodies thereto.

These antibodies can be, for example, polyclonal or monoclonal antibodies. The present invention also includes chimeric, single chain, and humanized antibodies, as well as Fab fragments, or the product of a Fab expression library. Various procedures known in the art may be used for the production of such antibodies and fragments.

Antibodies generated against $PLA_2$ can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide.

For preparation of monoclonal antibodies, any technique which provides antibodies produced by continuous cell line cultures can be used. Examples include the hybridoma technique (Kohler, G. and Milstein C., *Nature* 256:495–497 (1975)), the trioma technique, the human B-cell hybridoma technique (Kozbor et al., *Immunology Today* 4:72 (1983)) and the EBV-hybridoma technique to produce human monoclonal antibodies (Cole et al., pg. 77–96 in *MONOCLONAL ANTIBODIES AND CANCER THERAPY,* Alan R. Liss, Inc. (1985)).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic $PLA_2$.

Thus, among others, antibodies against $PLA_2$ may be employed to treat/inhibit various forms of cancer, including prostate cancer, and BPH.

$PLA_2$ BINDING MOLECULES AND ASSAYS $PLA_2$ could be used to isolate proteins which interact with it and this interaction could be a target for interference. Inhibitors of protein-protein interactions between $PLA_2$ and other factors could lead to the development of pharmaceutical agents for the modulation of $PLA_2$ activity. As used herein, the term "modulate" refer to affecting the $PLA_2$ function.

Thus, this invention also provides a method for identification of binding molecules to $PLA_2$. Genes encoding proteins for binding molecules to $PLA_2$ can be identified by numerous methods known to those of skill in the art, for example, ligand panning and FACS sorting. Such methods are described in many laboratory manuals such as, for instance, Coligan et al., Current Protocols in Immunology 1 (Rivett, A. J. *Biochem. J*. 291:1–10 (1993)): Chapter 5 (199 1).

For example, the yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, $PLA_2$ cDNA is fused to a Gal4 transcription factor DNA binding domain and expressed in yeast cells. cDNA library members obtained from cells of interest are fused to a transactivation domain of Gal4. cDNA clones which express proteins which can interact with $PLA_2$ will lead to reconstitution of Gal4 activity and transactivation of expression of a reporter gene such as Gal1-lacZ.

An alternative method is screening of λgt11, λZAP (Stratagene) or equivalent cDNA expression libraries with recombinant $PLA_2$. Recombinant $PLA_2$ protein or fragments thereof are fused to small peptide tags such as FLAG, HSV or GST. The peptide tags can possess convenient phosphorylation sites for a kinase such as heart muscle creatine kinase or they can be biotinylated. Recombinant $PLA_2$ can be phosphorylated with $^{32}[p]$ or used unlabeled and detected with streptavidin or antibodies against the tags. λgt11cDNA expression libraries are made from cells of interest and are incubated with the recombinant $PLA_2$, washed and cDNA clones isolated which interact with $PLA_2$. See, e.g., T. Maniatis et al, supra.

Another method is the screening of a mammalian expression library in which the cDNAs are cloned into a vector between a mammalian promoter and polyadenylation site and transiently transfected in COS or 293 cells followed by detection of the binding protein 48 hours later by incubation of fixed and washed cells with a labelled $PLA_2$, preferably iodinated, and detection of bound $PLA_2$ by autoradiography. See Sims et al, *Science* 241:585–589 (1988) and McMahan et al., *EMBO J*. 10:2821–2832 (1991). In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mamalian cells and panning the cells on a dish containing $PLA_2$ bound to the plate. Cells which attach after washing are lysed and the plasmid DNA isolated, amplified in bacteria, and the cycle of transfection and panning repeated until a single cDNA clone is obtained. See Seed et al, *Proc. Natl. Acad. Sci. USA* 84:3365 (1987) and Aruffo et al., *EMBO J*. 6:3313 (1987). If the binding protein is secreted, its cDNA can be obtained by a similar pooling strategy once a binding or neutralizing assay has been established for assaying supernatants from transiently transfected cells. General methods for screening supernatants are disclosed in Wong et al., *Science* 228:810–815 (1985).

Another alternative method is isolation of proteins interacting with $PLA_2$ directly from cells. Fusion proteins of $PLA_2$ with GST or small peptide tags are made and immobilized on beads. Biosynthetically labeled or unlabeled protein extracts from the cells of interest are prepared, incubated with the beads and washed with buffer. Proteins interacting with $PLA_2$ are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another alternative method is immunoaffinity purification. Recombinant $PLA_2$ is incubated with labeled or unlabeled cell extracts and immunoprecipitated with anti-$PLA_2$ antibodies. The immunoprecipitate is recovered with protein A-Sepharose and analyzed by SDS-PAGB. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method is screening of peptide libraries for binding partners. Recombinant tagged or labeled $PLA_2$ is used to select peptides from a peptide or phosphopeptide library which interact with $PLA_2$. Sequencing of the peptides leads to identification of consensus peptide sequences which might be found in interacting proteins.

$PLA_2$ binding partners identified by any of these methods or other methods which would be known to those of ordinary skill in the art as well as those putative binding partners discussed above can be used in the assay method of the invention. Assaying for the presence of $PLA_2$/binding partner complex are accomplished by, for example, the yeast two-hybrid system, ELISA or immunoassays using antibodies specific for the complex. In the presence of test substances which interrupt or inhibit formation of $PLA_2$/binding partner interaction, a decreased amount of complex will be determined relative to a control lacking the test substance.

Assays for free $PLA_2$ or binding partner are accomplished by, for example, ELISA or immunoassay using specific antibodies or by incubation of radiolabeled $PLA_2$ with cells or cell membranes followed by centrifugation or filter separation steps. In the presence of test substances which interrupt or inhibit formation of $PLA_2$/binding partner interaction, an increased amount of free $PLA_2$ or free binding partner will be determined relative to a control lacking the test substance.

Polypeptides of the invention also can be used to assess $PLA_2$ binding capacity of $PLA_2$ binding molecules in cells or in cell-free preparations.

AGONISTS AND ANTAGONIST—ASSAYS AND MOLECULES

The $PLA_2$ may be employed in a process for screening for compounds which either inhibit, promote or modulate the enzymatic activity of $PLA_2$. One standard assay for $PLA_2$ uses [linoleoyl-1-$^{14}$C] labeled L-α-1-acyl-2-linoleoylphosphatidylethanolamine as a substrate and follows the release of $^{14}$C labeled free fatty acid. This assay or others could be used to identify either agonists or antagonists of $PLA_2$.

Examples of potential $PLA_2$ antagonists are small molecules such as organic molecules or peptides, antibodies, or in some cases an oligonucleotide, which binds to $PLA_2$ and prevents enzymatic activity.

Potential antagonists also include small molecules or proteins which are closely related to the binding molecules of the $PLA_2$, e.g. a fragment of the binding molecules, which have lost biological function, and when bind to the $PLA_2$ polypeptide inhibit its activity. ("Binding molecules" as used herein refer to molecules that specifcally bind to or interact with $PLA_2$ polypeptide of the present invention. Included in the definition of binding molecules are other factors, co-factors, units or subunits which enhance $PLA_2$ activity or diminish it. Such binding molecules are a part of the present invention. Binding molecules also may be non-naturally occurring, such as antibodies and antibody-derived reagents that bind specifically to $PLA_2$.)

A potential antagonist also includes an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature $PLA_2$, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241:456 (1988); and Dervan et al., *Science*, 251:1360 (1991)), thereby preventing transcription and the production of $PLA_2$ polypeptide. The antisense RNA oligonucleotide hybridizes to the mRNA in vivo and blocks translation of the mRNA molecule into the $PLA_2$ polypeptide (antisense—Okano, *J. Neurochem.*, 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the $PLA_2$ polypeptide. Included in this delivery is by gene therapy.

Another potential antagonist is a small molecule which binds to the $PLA_2$ making it inaccessible to binding molecules (e.g. substrates) such that normal biological activity is prevented. Examples of small molecules include, but are not limited to, small peptides or peptide-like molecules and organic compounds.

$PLA_2$ are ubiquitous in the animal host and are responsible for many biological functions, including many pathologies. Accordingly, it is desirous to find compounds and drugs which can inhibit the function of a $PLA_2$.

This invention additionally provides a method of treating an abnormal condition related to an excess of $PLA_2$ activity, such as BPH and various forms of cancer, including prostate cancer, which comprises administering to a subject the inhibitor compounds (antagonists) as hereinabove described along with a pharmaceutically acceptable carrier in an amount effective to inhibit $PLA_2$ activity directly or by blocking binding of binding molecules to $PLA_2$ polypeptide.

COMPOSITION AND KITS

The compounds which inhibit such $PLA_2$, may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention further relates to pharmaceutical packs and kits comprising one or more containers filled with one or more of the ingredients of the aforementioned compositions of the invention.

ADMINISTRATION

Polypeptides and other compounds of the present invention may be employed alone or in conjunction with other compounds, such as therapeutic compounds.

The pharmaceutical compositions may be administered in any effective, convenient manner including for instance, admninistration by topical, oral, anal, vaginal, intravenous, intraperitoneal, intramuscular, subcutaneous, intranasal or intradermal routes, among others.

The pharmaceutical compositions generally are administered in an amount effective for treatment or prophylaxis of a specific indication or indications. In general, the compositions are administered in an amount of at least about 10 µg/kg body weight. In most cases they will be administered in an amount not in excess of about 8 mg/kg body weight per day. Preferably, in most cases, dose is from about 10 µg/kg to about 1 mg/kg body weight, daily. It will be appreciated that optimum dosage will be determined by standard methods for each treatment modality and indication, taking into account the indication, its severity, route of administration, complicating conditions and the like.

VACCINE

Another aspect of the invention relates to a method for inducing an immunological response in an animal, particularly in a mammal, which comprises inoculating the animal with $PLA_2$, or a fragment or variant thereof, adequate to produce antibody to protect said animal from BPH or various forms of cancer, including prostate cancer. Yet another aspect of the invention relates to a method of inducing immunological response in an animal which comprises, through gene therapy, delivering gene encoding $PLA_2$, or a fragment or a variant thereof, for expressing $PLA_2$, or a fragment or a variant thereof in vivo in order to induce an immunological response to produce antibody to protect said animal from disease.

Further aspect of the invention relates to an immunological composition which, when introduced into an animal, particularly mammalian host, induces an immnunological response in that animal to a given $PLA_2$ gene or protein coded therefrom, wherein the composition comprises a recombinant $PLA_2$ gene or protein coded therefrom comprising DNA which codes for and expresses an antigen of said $PLA_2$ gene or protein coded therefrom.

The $PLA_2$ or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

The present invention also includes a vaccine formulation which comprises the immunogenic recombinant protein together with a suitable carrier. Since the protein may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain antioxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Whilst the invention has been described with reference to $PLA_2$, it is to be understood that this covers fragments of the naturally occurring protein and similar proteins (for example, having sequence homologies of 50% or greater) with additions, deletions or substitutions which do not substantially affect the immunogenic properties of the recombinant protein.

The present invention also provides a method for the production of transgenic animals with altered $PLA_2$ levels for the productions of animals bearing $PLA_2$ induced diseases. Transgenic, non-human, animals may be obtained by transfecting appropriate fertilized eggs or embryos of a host with nucleic acids encoding the $PLA_2$ disclosed herein, see for example U.S. Pat. Nos. 4,736,866; 5,175,385; 5,175,384 and 5,175,386. The resultant transgenic animal may be used as a model for the study of altered $PLA_2$ levels. Particularly, useful transgenic animals are those which display a detectable phenotype associated with the altered expression of the $PLA_2$ polypeptide. Drugs may then be screened for their ability to reverse or exacerbate the relevant phenotype.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

All examples are carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989), herein referred to as "Sambrook". All parts or amounts set out in the following examples are by weight, unless otherwise specified.

Unless otherwise stated size separation of fragments in the examples below is carried out using standard techniques of agarose and polyacrylamide gel electrophoresis ("PAGE") in Sambrook and numerous other references such as, for instance, by Goeddel et al., *Nucleic Acids Res.* 8:4057 (1980).

Example 1 mRNA is prepared from normal and cancerous prostate tissue, size fractionated on an agarose gel and then transferred to a nylon membrane (northern blot). This blot is then hybridized to a $PLA_2$ specific cDNA probe that has been labeled with radioactive $[^{32}P]$-dCTP. Following incubation, the blot is then washed under stringent conditions (described in Sambrook) and then exposed to film. Changes in mRNA levels as a function of disease will be seen as a change in intensity of the signal seen in diseased versus normal tissue.

Example 2

Below are the results from the $PLA_2$ levels in serum as found by an ELISA assay.

A. Normal healthy men without prostate disease (17 individuals): 4.85 ng/ml±3.29

B. Normal healthy women (20 individuals): 5.31 ng/ml±3.44

C. Combined normal healthy men and women (37 individuals): 5.11 ng/ml±3.33

D. Patients with progressive prostate cancer (10 individuals): 32.65 ng/ml ±18.7

Eight (80%) of ten patients with progressive prostate cancer had $PLA_2$ blood levels at least three standard deviations above the combined mean of normal healthy men and women.

E. Patients with prostate cancer in remission (10 individuals): 7.77 ng/ml±8.67

Only one of nine (11.1%) patients with prostate cancer in remission had $PLA_2$ blood levels at least three standard deviations above the combined mean of normal healthy men and women.

F. Patients with stabilized prostate cancer (5 individuals): 8.74 na/ml±8.12

Only one of five patients (20%) with stable prostate cancer had $PLA_2$ blood levels at least three standard deviations above the combined mean of normal healthy men and women.

G. Patients with benign prostate hypertrophy (13 individuals): 4.59 ng/ml±3.29

No patients with benign prostate hypertrophy had $PLA_2$ blood levels at least three standard deviations above the combined mean of normal healthy men and women.

H. Patients with prostatitis (7 individuals): 8.47 ng/ml±9.73

Only one of seven (14.3%) patients with prostatitis had $PLA_2$ blood levels at least three standard deviations above the combined mean of normal healthy men and women.

What is claimed is:

1. A method of diagnosing prostate cancer in a patient comprising measuring PLA2 protein levels in said patient wherein PLA2 protein levels at least two fold greater than PLA2 protein levels in normal controls are indicative of prostate cancer.

\* \* \* \* \*